United States Patent [19]

Hardy et al.

[11] 4,293,467

[45] Oct. 6, 1981

[54] ISOPROPYLIDENEDICYCLOHEXYLENE ESTERS AND THEIR USE AS LIGHT STABILIZERS

[75] Inventors: William B. Hardy, Bound Brook; Frank F. Loffelman, Bridgewater, both of N.J.

[73] Assignee: American Cyanamid Company, Stamford, Conn.

[21] Appl. No.: 112,390

[22] Filed: Jan. 16, 1980

[51] Int. Cl.³ .................. C07D 401/12; C08K 5/34
[52] U.S. Cl. ..................... 260/45.8 N; 260/23 H; 260/45.85 B; 260/45.95 H; 546/189
[58] Field of Search ............... 260/45.8 NP; 546/189

[56] References Cited

U.S. PATENT DOCUMENTS 4,064,102 12/1977 Hillard .................. 260/45.8 NP
4,130,710 12/1978 Cook .................... 260/45.8 NP

*Primary Examiner*—Howard E. Schain
*Assistant Examiner*—R. A. White
*Attorney, Agent, or Firm*—Bruce F. Jacobs

[57] ABSTRACT

Isopropylidenedicyclohexylene esters of 2,2,6,6-tetramethylpiperidine-4-carboxylic acid are disclosed as well as their use as light stabilizers for thermoplastic polymers such as polypropylene.

16 Claims, No Drawings

ISOPROPYLIDENEDICYCLOHEXYLENE ESTERS AND THEIR USE AS LIGHT STABILIZERS

This invention relates to esters of 2,2,6,6-tetramethyl-piperidine-4-carboxylic acid, and more particularly to esters represented by formula (I):

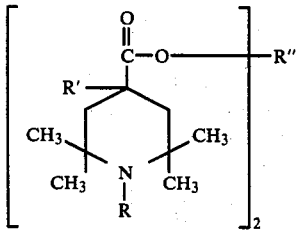

wherein R is hydrogen or alkyl ($C_1$-$C_8$); R' is hydrogen, hydroxyl or alkoxy ($C_1$-$C_8$); and R" is a group represented by the structure:

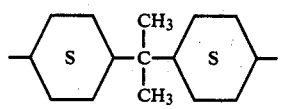

Preferred esters of the invention are those wherein R is hydrogen or methyl; and R' is hydrogen.

This invention also relates to the use of these esters as stabilizers against photo- and thermo-oxidative degradation, particularly against degradation caused by UV light, of synthetic polymers especially polyolefins, and most especially polyethylene and polypropylene. The invention further relates to polymer compositions stabilized by the incorporation therein of said esters.

Stabilizers for synthetic and naturally occurring polymers, including UV stabilizers, have been the subject of continuing investigation for many years, and numerous compounds have been suggested for such purpose. Recent patent literature has described a considerable number of stabilizer compounds which are derivatives of hindered amines of the type:

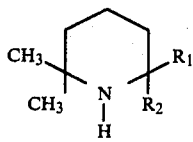

wherein $R_1$ and $R_2$ may be the same or different and represent an alkyl of 1 to 4 carbon atoms. Of particular interest is 2,2,6,6-tetramethylpiperidine and its derivatives.

U.S. Pat. No. 3,640,928 (Murayama to Sankyo Company, Ltd.) particularly describes esters, and their use in stabilizing polymers of the type represented by formula:

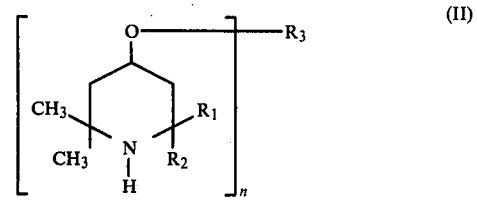

wherein $R_1$ and $R_2$ are as defined above; $R_3$ is an acyl, diacyl, or triacyl group derived from aliphatic, alicyclic, or heterocyclic mono-, di-, or tricarboxylic acids; n=1-3.

U.S. Pat. No. 4,064,102 (Hillard et al. to American Cyanamid Company) and a copending reissue application thereof, U.S. Ser. No. 057,786, now U.S. Pat. Re No. 30385 disclose that esters of formula (I), wherein R is hydrogen or alkyl ($C_1$-$C_8$); R' is hydrogen, hydroxyl, or alkoxy ($C_1$-$C_8$); R" is alkylene ($C_2$-$C_{12}$), or cycloalkylene; and n=2, provide superior stabilizing properties against photodegradation of synthetic polymers, particularly polypropylene, as compared with the esters of formula (II). More especially, esters of formula (I) wherein R is hydrogen or alkyl ($C_1$-$C_8$); R' is hydrogen or lower alkoxy ($C_1$-$C_8$); R" is one of groups:

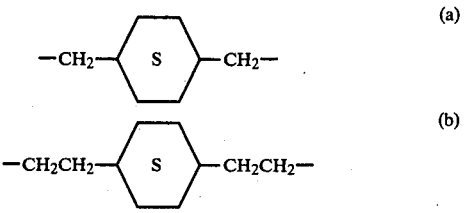

and n=2, exhibit superior light stabilizing properties.

The present invention represents a further improvement over the compounds of Hillard et al. in that, in addition to exhibiting superior light stabilizing properties, the compounds confer superior thermo-oxidative protection to the polymers, are non-blooming, i.e., they do not exude to the surface of the polymer, and are significantly less extractable, or non-extractable, from the polymer by dry cleaning solvents (tetrachloroethylene) or aqueous detergent solutions.

In the above formula (I) when R is methyl and R' is hydrogen, photo-oxidative stability of polymers containing the compound is exceptional as shown by Example 3D below.

The compounds of the present invention are readily prepared by methods described by Hillard et al., incorporated herein by reference, using as the diol the compound isopropylidene bis(1,4-cyclohexanol),

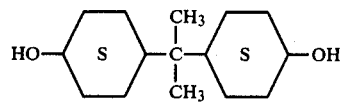

which is obtained by hydrogenation of isopropylidene bisphenol (commonly referred to as bisphenol A).

The term "synthetic polymer," as used herein, is intended to include polyolefins, and particularly polyalpha-olefins, such as polyethylene, polypropylene, polybutylene, and copolymers thereof, for example, ethylene-propylene copolymers. Also intended are polyolefins such as polystyrene, polybutadiene, polyisoprene, and the like, and copolymers, such as ethylene-vinylacetate copolymers, styrene-butadiene copolymers, acrylonitrile-butadiene-styrene polymers (ABS plastics), and polyurethanes. The invention is particularly directed to the stabilization of polypropylene.

The compounds of the invention are incorporated into the polymer substrate by any of the various standard procedures commonly used in the art, at any stage prior to the manufacture of shaped articles therefrom, including filaments, fiber, yarn, film, sheet, other molded articles, and the like.

The amount of the compounds of the invention, which may be incorporated into the polymer, may vary widely depending on the type, properties, and particular uses of the polymer to be stabilized. In general, they may be added in amounts ranging from about 0.01 to 5% by weight based on the polymer, preferably about 0.01 to 2% and, still more preferably, 0.01 to 1% by weight.

The compounds may be used alone or in combination with other known stabilizers, such as antioxidants and UV absorbers, fillers, or other compounding ingredients commonly used, especially processing antioxidants.

In the following non-limiting examples, all parts and percents are by weight unless otherwise specified.

EXAMPLE 1

Preparation of Isopropylidenedi-4,1-cyclohexylene 2,2,6,6-tetramethyl-4-piperidenecarboxylate Ethyl 2,2,6,6-tetramethyl-4-piperidenecarboxylate (30 grams, 0.1408 mole), 16.93 grams, 0.070 mole, of 1,1'-isopropylidene bis(4-hydroxycyclohexane), 60 ml. of Isopar M (high-boiling isoparaffin solvent) and 0.15 gram of Fastcat 4201 (alkyl tin esterification catalyst-M&T Chemical Co.) were heated with stirring to 230° C. over a period of 90 minutes. The mixture was heated for one hour at 230°-240° C., during which time 18 ml. of ethanol distilled off. The reaction mixture was dissolved in 250 ml. of hexane, filtered, and then saturated with gaseous hydrogen chloride. The solid precipitate was dissolved in chloroform and washed with one equivalent of sodium carbonate solution. The alkaline washes were extracted with chloroform and the chloroform extracts combined, dried over magnesium sulfate, and evaporated to dryness. The resulting amber oil was slurried in acetonitrile to give a white solid, which was recrystallized twice from acetonitrile; melting point 165°-167° C.

EXAMPLE 2

Preparation of Isopropylidenedi-4,1-cyclohexylene 1,2,2,6,6-pentamethyl-4-piperidenecarboxylate A mixture of the product of Example 1 (8 grams, 0.027 mole), and 2.2 grams (2 ml.) of formaldehyde solution was stirred and 3.3 ml. of formic acid was added dropwise. The mixture was then refluxed for about 16 hours. The resulting syrup was cooled to room temperature and dissolved in 150 ml. of water. Sodium hydroxide (5 N) was added to a pH of 11.5. The mixture was extracted with methylene chloride, the extracts dried over magnesium sulfate, and evaporated to dryness. The residue (6 grams) was recrystallized from 80 ml. of isopropanol to give 5.2 grams of white needles, melting point 193.5°-195.5° C.

EXAMPLE 3

Unstabilized polypropylene (100 parts by weight) was dry blended with 0.05 part by weight of each of 2,6-t.butyl-p-cresol and octadecyl 3,5-di-t.butyl-4-hydroxy hydrocinnamate (both processing antioxidants) and 0.1 part by weight of calcium stearate. The blended dry powder was extruded into multifilament at a maximum temperature of 227° C. The pellets were re-extruded into a 250-denier/30-filament fiber (8.3 denier/filament) at a maximum temperature of 265° C. This represents the control fiber.

In a similar manner, multifilament was spun containing, in addition to the processing antioxidants and calcium stearate, 0.25 part by weight of the additive light stabilizer compounds described below.

Woven polypropylene multifilament samples were prepared consisting of 1×10 plain-weave fabric having a 20/2 Orlon warp (40 ends/inch) and polypropylene multifilament fill (40 picks/inch), the center 2 inches of the fabric being void of warp yarn (Orlon). The samples were then exposed in a forced draft oven at 120° C. with a small (35 gram) weight attached to the ends of the strips. Embrittlement (failure) was measured by the spontaneous fall of the weight when the polypropylene reached the point of failure. Failure is reported in days exposure at 120° C.

The additives tested are as follows:

A. 1,4-cyclohexylenedimethylene 2,2,6,6-tetramethyl-4-piperidinecarboxylate
B. 1,4-cyclohexylenedimethylene 1,2,2,6,6-pentamethyl-4-piperidinecarboxylate
C. isopropylidenedi-4,1-cyclohexylene 2,2,6,6-tetramethyl-4-piperidinecarboxylate
D. isopropylidenedi-4,1-cyclohexylene 1,2,2,6,6-pentamethyl-4-piperidinecarboxylate.

Compounds A and B are the closest prior art compounds of Hillard et al. while Compounds C and D are compounds within the scope of the present invention. As is readily apparent from the Table, the compounds of this invention are far superior to the closest prior art. In particular, Compound D is more than three times as effective as the corresponding prior art Compound B.

TABLE

Thermo-oxidative Stability of Polypropylene Multifilament Compositions at 120° C.

| Example No. | Additive | Conc., % | Failure Time (Days) |
|---|---|---|---|
| 1 | None* | — | 4 |
| 2 | A | 0.25 | 8 |
| 3 | B | 0.25 | 7 |
| 4 | C | 0.25 | 14 |
| 5 | D | 0.25 | 25 |

*contains only processing antioxidants and calcium stearate

What is claimed is:

1. A compound represented by the formula

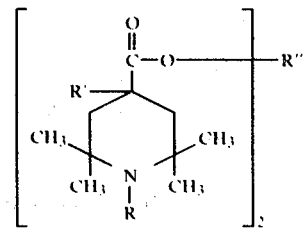

wherein R is hydrogen or alkyl ($C_1$–$C_8$); R' is hydrogen, hydroxyl or alkoxy ($C_1$–$C_8$); and R" is the group:

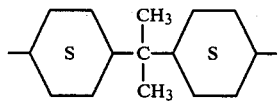

2. The compound of claim 1 wherein R is hydrogen or methyl; and R' is hydrogen.

3. The compound of claim 1 which is isopropylidene-di-4,1-cyclohexylene 2,2,6,6-tetramethyl-4-piperidinecarboxylate.

4. The compound of claim 1 which is isopropylidenedi-4,1-cyclohexylene 1,2,2,6,6-pentamethyl-4-piperidinecarboxylate.

5. A composition comprising a synthetic polymer subject to oxidative degradation and an effective stabilizing amount of a compound represented by the formula

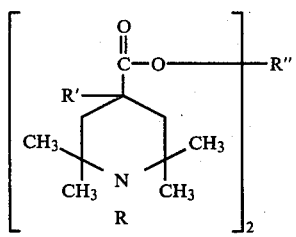

wherein R is hydrogen or alkyl ($C_1$–$C_8$); R' is hydrogen, hydroxyl or alkoxy ($C_1$–$C_8$); and R" is the group:

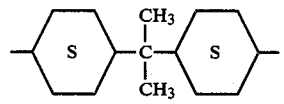

6. The composition of claim 5 wherein the polymer is a poly-alpha-olefin.

7. The composition of claim 6 wherein the poly-alpha-olefin is polypropylene.

8. The composition of claim 5 wherein the polymer is a polypropylene multifilament.

9. The composition of claim 5 wherein the effective amount is about 0.01 to 5% by weight based on the polymer.

10. The composition of claim 5 wherein the effective amount is about 0.01 to 1% by weight based on the polymer.

11. The composition of claims 5, 7 or 10 wherein R is hydrogen or methyl and R' is hydrogen.

12. A method of stabilizing a synthetic polymer subject to oxidative degradation comprising adding thereto a stabilizing effective amount of a compound represented by the formula:

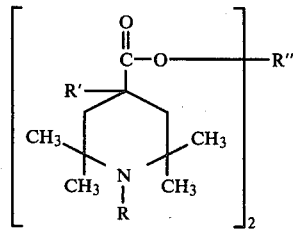

wherein R is hydrogen or alkyl ($C_1$–$C_8$); R' is hydrogen, hydroxyl or alkoxy ($C_1$–$C_8$) and R" is the group:

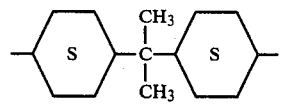

13. The method of claim 12 wherein R is hydrogen or methyl and R' is hydrogen.

14. The method of claim 12 wherein the polymer is a poly-alpha-olefin.

15. The method of claim 14 wherein the poly-alpha-olefin is polypropylene.

16. The method of claim 12 wherein the effective amount is about 0.01 to 5% by weight based on the polymer.

* * * * *